United States Patent [19]

Nagai et al.

[11] Patent Number: 5,602,280
[45] Date of Patent: Feb. 11, 1997

[54] PROCESS FOR PRODUCTION OF UNSATURATED ALDEHYDE AND UNSATURATED CARBOXYLIC ACID

[75] Inventors: Koichi Nagai, Niihama; Yoshisaburou Nomura, Ehime-ken; Yoshihiko Nagaoka, Niihama, all of Japan

[73] Assignee: Sumitomo Chemical Company, Limited, Osaka, Japan

[21] Appl. No.: 266,190

[22] Filed: Jun. 27, 1994

[30] Foreign Application Priority Data

Jun. 25, 1993 [JP] Japan ................................ 5-154885
Dec. 13, 1993 [JP] Japan ................................ 5-312267

[51] Int. Cl.⁶ .................................................. C07C 51/16
[52] U.S. Cl. ..................... 562/546; 562/538; 562/547; 562/577; 562/599; 502/38
[58] Field of Search ............................. 562/577, 599, 562/538, 546, 547; 502/38

[56] References Cited

U.S. PATENT DOCUMENTS

| | | | |
|---|---|---|---|
| 3,790,502 | 2/1974 | Nemec et al. | |
| 3,882,159 | 5/1975 | Callahan et al. | 260/465.3 |
| 4,425,255 | 1/1984 | Toyoda et al. | 502/38 |
| 4,709,070 | 11/1987 | Sasaki et al. | 558/322 |
| 4,757,038 | 7/1988 | Sasaki et al. | 502/20 |
| 5,276,178 | 1/1994 | Onodera et al. | 562/537 |

FOREIGN PATENT DOCUMENTS

| | | |
|---|---|---|
| 0109774 | 5/1984 | European Pat. Off. . |
| 0468290 | 1/1992 | European Pat. Off. . |
| 2241516 | 3/1975 | France . |
| 3006894 | 9/1980 | Germany . |
| 34-193136 | 1/1959 | Japan . |

*Primary Examiner*—Gary Geist
*Assistant Examiner*—Rosalynd A. Williams
*Attorney, Agent, or Firm*—Sughrue, Mion, Zinn, Macpeak & Seas

[57] ABSTRACT

Disclosed are a process for producing an unsaturated aldehyde and an unsaturated carboxylic acid which comprises subjecting propylene, isobutylene or tertiary butanol to gas phase catalytic oxidation with molecular oxygen in the presence of (i) a catalyst comprising composite oxide of the formula $Mo_aBi_bFe_cA_dB_eC_fD_gO_x$ and (ii) a molybdenum oxide which in itself is substantially inert to the gas phase catalytic oxidation; a process for reusing the catalyst deteriorated due to the gas phase catalytic oxidation after mixing it with the molybdenum oxide; and a method of regenerating the deteriorated catalyst by mixing it with the molybdenum oxide.

29 Claims, No Drawings

PROCESS FOR PRODUCTION OF UNSATURATED ALDEHYDE AND UNSATURATED CARBOXYLIC ACID

FIELD OF THE INVENTION

This invention relates to a process for producing an unsaturated aldehyde and an unsaturated carboxylic acid by gas-phase catalytic oxidation of propylene, isobutylene or tertiary butanol. More particularly, this invention relates to a method of inhibiting the performance deterioration or degeneration of the catalyst for use in said process, to a method for reuse of the deteriorated catalyst, and to a method of regenerating the deteriorated catalyst.

BACKGROUND OF THE INVENTION

The production of acrolein and acrylic acid from propylene and the production of methacrolein and methacrylic acid from isobutylene or tertiary butanol by the gas-phase catalytic oxidation reaction using the so-called molybdenum-bismuth composite oxide catalyst, and the production of acrylonitrile or methacrylonitrile by the gas-phase catalytic ammoxidation using the same catalyst are well known. However, when the reaction is continued in a long production run, this catalyst suffers deterioration or degeneration so that the conversion and selectivity of the reaction are lowered with time.

Several technologies are known for controlling the deterioration of the composite oxide catalyst. Japanese Unexamined Patent Publication (Kokai) No. 59-193136, for instance, proposes a method which comprises a molybdenum oxide-bearing substance prepared by supporting molybdenum oxide on an inert heat-resisting inorganic substance, and Japanese Examined Patent Publication (Kokoku) No. 63-38331 proposes a method in which a plurality of molybdenum-bismuth multi-component catalysts prepared with a gradient of activity by varying the kinds and/or amounts of alkali metal and thallium group elements in the molybdenum-bismuth multi-component catalyst are arranged in an increasing order of activity from the reactant gas inlet side to the outlet side of a reactor.

Japanese Examined Patent Publication (Kokoku) No. 53-30688 proposes a method in which the catalyst is diluted with an inert substance and packed in such a manner that the catalyst activity increases either continuously or stepwise to 100% in the direction of flow of the reactant gas, viz. from the inlet to the outlet of a reactor.

However, Japanese Unexamined Patent Publication (Kokai) No. 59-193136 has the disadvantage that the catalyst must be supported on an inert heat-resisting inorganic carrier and, moreover, the selectivity of the desired compound according to the process disclosed therein is not sufficiently high for commercial use.

The technologies disclosed in Japanese Examined Patent Publications (Kokoku) Nos. 63-38331 and 53-30688, which are intended to control the catalyst activity by varying the composition of the catalyst or diluting the catalyst to avoid local temperature rise, are capable of suppressing to some extent the loss of molybdenum from the catalyst which is a cause of catalyst deterioration but do not provide for long-term inhibition of catalyst deterioration. Thus, these prior art technologies are not sufficiently satisfactory for practicing on a commercial scale.

Several methods have also been proposed for enabling the reuse or regeneration of the composite oxide catalyst deteriorated in a prolonged course of reaction.

By way of example, Japanese Unexamined Patent Publication (Kokai) No. 55-67335 describes a method which comprises subjecting a deteriorated composite oxide catalyst to a heat treatment in an inert atmosphere at a temperature between 500° C. and 800° C., and Japanese Unexamined Patent Publication (Kokai) No. 57-56044 discloses a method which comprises subjecting a deteriorated composite oxide catalyst to a heat treatment in a reducing atmosphere at a temperature between 200° C. and 700° C. and then calcining the catalyst in a molecular oxygen-containing atmosphere at a temperature between 550° C. and 700° C.

However, these methods are primarily intended for the treatment of the catalysts used in ammoxidation and, therefore, when the high-temperature calcination procedure disclosed is applied to a catalyst for the partial oxidation of propylene, isobutylene or tertiary butanol, the catalyst tends to be sintered with the resultant decrease in activity.

Referring to the catalyst for use in the partial oxidation of propylene or isobutylene, Japanese Unexamined Patent Publication (Kokai) No. 61-33234 proposes a heat treatment at 380° C.–540° C. in an atmosphere substantially composed of air, and Japanese Unexamined Patent Publication (Kokai) No. 63-137755 discloses a heat treatment at 300° C.–500° C. in the presence of an oxidizing gas containing both molecular oxygen and steam. Furthermore, Japanese Unexamined Patent Publication (Kokai) No. 5-184945 discloses a method in which 2–10 weight % of the deteriorated catalyst is withdrawn from the reactant gas inlet region and the remainder of the deteriorated catalyst is heat-treated at 300°–500° C. in a molecular oxygen-containing gaseous atmosphere for regeneration.

However, these methods for catalyst regeneration by heat treatment are not sufficiently effective, and as disclosed in Japanese Unexamined Patent Publication (Kokai) No. 5-184945, the severely deteriorated portion of the catalyst in the vicinity of the reactant gas inlet can hardly be regenerated. Moreover, repeated regeneration is impossible.

It is known that the dissipation of molybdenum is a cause of catalyst deterioration and, therefore, it has been proposed to compensate for the loss of molybdenum by certain means for the purpose of regenerating the catalyst. Japanese Unexamined Patent Publication (Kokai) No. 50-49201 describes a regeneration method in which the catalyst is contacted with fluidized particles of a substantially inert molybdenum-containing carrier. Japanese Unexamined Patent Publication (Kokai) No. 52-131989 describes a method for catalyst regeneration in which the deteriorated catalyst is saturated with a solution containing at least molybdenum and bismuth and then calcined, and Japanese Unexamined Patent Publication (Kokai) No. 57-56044 discloses a method which comprises adding a molybdenum compound to the deteriorated composite oxide catalyst, heat-treating the mixture at 200°–700° C. in a reducing atmosphere and further calcining the heat-treated catalyst at 550°–700° C. in a molecular oxygen-containing atmosphere.

However, all of these methods are mainly concerned with the regeneration of the catalyst for the ammoxidation of propylene, which is used at a high temperature. Thus, in the processes described in Japanese Unexamined Patent Publication (Kokai) Nos. 50-49201 and 52-131989, the selectivity of the fixed-bed partial oxidation reaction of propylene, isobutylene or tertiary butanol with the regenerated catalyst is not as high as satisfactory. In the process disclosed in Japanese Unexamined Patent Publication (Kokai) No. 57-56044, the regenerated catalyst tends to be sintered to detract from catalytic activity.

3

An object of this invention is, therefore, to provide a method for inhibiting deterioration of the high-activity catalyst used in the production of an unsaturated aldehyde and unsaturated carboxylic acid by the gas-phase catalytic oxidation of propylene, isobutylene or tertiary butanol, a method for reuse of the so-deteriorated catalyst, and a method of regenerating the catalyst.

This and other objects will be apparent from the following description.

SUMMARY OF THE INVENTION

The inventors of this invention made extensive researches on the causes of deterioration of the catalyst used in the gas-phase catalytic oxidation of propylene, isobutylene or tertiary butanol for the production of the corresponding unsaturated aldehyde and unsaturated carboxylic acid, on the method for using the catalyst and on the method for regenerating the deteriorated catalyst, and consequently discovered that the above objects of this invention can be accomplished by conducting the reaction in the presence of said composite oxide catalyst and a molybdenum oxide which in itself is substantially inert to the reaction, or by reusing the deteriorated catalyst after blending it with molybdenum oxide which in itself is substantially inert to the reaction. This invention has been made on the basis of the above findings.

Thus, this invention provides a process for producing an unsaturated aldehyde and an unsaturated carboxylic acid by the gas-phase catalytic oxidation of propylene, isobutylene or tertiary butanol with molecular oxygen in the presence of a catalyst comprising composite oxide represented by the formula $$Mo_aBi_bFe_cA_dB_eC_fD_gO_x \qquad (1)$$

wherein Mo, Bi, Fe and O represent molybdenum, bismuth, iron and oxygen, respectively; A represents nickel and/or cobalt; B represents at least one element selected from the group consisting of manganese, zinc, calcium, magnesium, tin and lead; C represents at least one element selected from the group consisting of phosphorus, boron, arsenic, tellurium, tungsten, antimony and silicon; D represents at least one element selected from the group consisting of potassium, rubidium, cesium and thallium; in case of a being 12, $0<b\leq10$, $0<c\leq10$, $1\leq d\leq10$, $0\leq e\leq10$, $0\leq f\leq20$ and $0<g\leq2$, and x has a value dependent on the oxidation state of the respective elements, characterized in that the gas-phase catalytic oxidation reaction is conducted in the presence of said catalyst and a molybdenum oxide which in itself is substantially inert to the gas-phase catalytic oxidation reaction.

This invention also provides a process for producing an unsaturated aldehyde and an unsaturated carboxylic acid by the gas-phase catalytic oxidation of propylene, isobutylene or tertiary butanol with molecular oxygen in the presence of a catalyst comprising composite oxide represented by the formula (1), characterized in that the gas-phase catalytic oxidation is conducted in the presence of a mixture of the catalyst deteriorated by the gas phase catalytic oxidation and a molybdenum oxide which in itself is substantially inert to said gas-phase catalytic oxidation.

In other words, the present invention provides a process for producing an unsaturated aldehyde and an unsaturated carboxylic acid, comprising the steps of (i) subjecting propylene, isobutylene or tertiary butanol to gas-phase catalytic oxidation with molecular oxygen in the presence of a catalyst comprising composite oxide represented by the formula (1) until the catalyst is deteriorated, and (ii) further conducting the gas-phase catalytic oxidation with molecular oxygen in the presence of a mixture of the thus deteriorated catalyst and a molybdenum oxide which in itself is substantially inert to said gas-phase catalytic oxidation.

The present invention further provides a process for regenerating a catalyst comprising composite oxide represented by the formula (1) which has been used in, and deteriorated due to, a gas-phase catalytic oxidation of propylene, isobutylene or tertiary butanol with molecular oxygen, the process comprising the step of mixing the deteriorated catalyst with a molybdenum oxide which in itself is substantially inert to said gas-phase catalytic oxidation.

DETAILED DESCRIPTION OF THE INVENTION

This invention finds application in processes for the production of acrolein and acrylic acid by gas phase catalytic oxidation of propylene with molecular oxygen and for the production of methacrolein and methacrylic acid by gas phase catalytic oxidation of isobutylene or tertiary butanol with molecular oxygen.

The catalyst used in these processes comprises composite oxide represented by the following formula:

$$Mo_aBi_bFe_cA_dB_eC_fD_gO_x \qquad (1)$$

wherein Mo, Bi, Fe and O represent molybdenum, bismuth, iron and oxygen, respectively; A represents nickel and/or cobalt; B represents at least one element selected from the group consisting of manganese, zinc, calcium, magnesium, tin and lead; C represents at least one element selected from the group consisting of phosphorus, boron, arsenic, tellurium, tungsten, antimony and silicon; D represents at least one element selected from the group consisting of potassium, rubidium, cesium and thallium; a, b, c, d, e, f, g and x represent, respectively, the number of atoms of Mo, Bi, Fe, A, B, C, D and O, and when a is 12, $0<b\leq10$, $0<c\leq10$, $1\leq d\leq10$, $0\leq e\leq10$, $0\leq f\leq20$ (or $0\leq f\leq10$) and $0<g\leq2$, and x has a value dependent on the oxidation state of the respective elements.

Hereinafter the term "the catalyst comprising composite oxide represented by the formula (1)" may sometimes be referred to simply as "said catalyst".

Composite oxides of the above formula (1) are described in U.S. Pat. No. 3,642,685, U.S. Pat. No. 3,799,978, U.S. Pat. No. 3,778,386 and U.S. Pat. No. 3,970,702, among others. The preferred composite oxide include, for example, the following.

$$Mo_{12}Bi_{0.1-5}Fe_{0.5-5}Co_{5-10}Cs_{0.01-1}Si_{0.1-20}$$

$$Mo_{12}W_{0.1-2}Bi_{0.1-5}Fe_{0.5-5}Co_{5-10}Cs_{0.01-1}Si_{0.1-20}$$

$$Mo_{12}W_{0.1-2}Bi_{0.1-5}Fe_{0.5-5}Co_{5-10}K_{0.01-1}Si_{0.1-20}$$

$$Mo_{12}Bi_{0.1-5}Fe_{0.5-5}Co_{5-10}Tl_{0.01-1}P_{0.01-2}Si_{0.1-20}$$

and $$Mo_{12}Bi_{0.1-5}Fe_{0.5-5}Ni_{5-10}Tl_{0.01-1}P_{0.01-2}Si_{0.1-20}.$$

In the above examples, the number of oxygen atoms is decided depending on the oxidation states of the other elements, and therefore the oxygen (O) is not shown in the formulas.

For use as said catalyst, the composite oxide of the formula (1) may be used as it is or as carried on a support such as α-alumina or as mixed with inorganic fibers such as glass fibers, ceramic fibers, whiskers, etc.

The reaction is generally carried out using a fixed-bed reactor for commercial purposes and such fixed-bed reactors are generally multi-tubular reactors. These reactors may be those conventionally used in the art.

In the process for producing an unsaturated aldehyde and unsaturated carboxylic acid by the gas phase catalytic oxidation of propylene, isobutylene or tertiary butanol with molecular oxygen in the presence of said catalyst, the deterioration of the catalyst usually occurs when the catalyst is used for a period of time for the gas phase catalytic oxidation reaction, with the result that the conversion and the selectivity of the desired product decreases as the reaction time increases. When the reaction is conducted in the presence of said catalyst and a molybdenum oxide which in itself is substantially inert to the gas phase catalytic oxidation reaction (hereinafter this term may sometimes be referred to simply as "said molybdenum oxide"), the deterioration of said catalyst is inhibited for a remarkably longer period of time than when the reaction is conducted in the absence of said molybdenum oxide.

Said molybdenum oxide for use in accordance with this invention is preferably molybdenum trioxide. However, there is no particular restriction on the type of said molybdenum oxide insofar as it is substantially inert in itself to the gas phase catalytic oxidation reaction, and generally the one having a specific surface area of not more than about 2 $m^2/g$ measured by BET method or the one having an average particle size of not smaller than about 1 μm measured by light scattering particle size analyzer can be mentioned. In order to evaluate the inertness of a particular molybdenum oxide and to decide whether it can be used in the reaction of this invention, it may be a good way to carry out the above-mentioned reaction using the molybdenum oxide in question in place of said catalyst. When the molybdenum oxide in question is substantially inert to the gas phase catalytic oxidation reaction, it can be used in the present invention.

The molybdenum oxide which can be substantially inert to the reacton can be prepared, for example, by calcining a commercially available molybdenum compound such as ammonium molybdate, molybdenum trioxide or the like in air using a box furnace, rotary kiln or other furnace at a temperature of about 550°–700° C. for 1–10 hours. The molybdenum oxide calcined at a temperature lower than 550° C. in the usual manner has an ability to oxidize olefins and when such molybdenum oxide is used in combination with said catalyst, the selectivity tends to be sacrificed. Of course, any molybdenum oxide that is already substantially inert, for example the one having a specific surface area of not more than about 2 $m^2/g$ measured by BET method or the one having an average particle size of not smaller than about 1 μm measured by a light scattering particle size analyzer, need not be calcined and such a molybdenum oxide may be selected from among the commercially available molybdenum oxides.

The expression "a molybdenum oxide in itself is substantially inert to the gas phase catalytic oxidation" means that, where the gas phase oxidation reaction in the presence of a fresh catalyst comprising composite oxide represented by the formula (1) achieves a conversion of 95–100%, the conversion obtainable by conducting the gas phase oxidation reaction using said molybdenum oxide in question alone in the same amount as said catalyst under otherwise the same reaction conditions is generally not more than 10%, preferably not more than 5% and still more preferably not more than 2%.

There is no particular limitation on the manner how said molybdenum oxide is present together with said catalyst. For example, there may be mentioned a method which comprises molding the molybdenum oxide singly or in combination with an inert carrier such as silica by compression, extrusion or impregnation, mixing the molded molybdenum oxide with said catalyst which is also molded, and filling a reactor with the resultant mixture. An alternative method comprises blending a powder of said molybdenum oxide with a powder of said catalyst, molding the resultant blend by compression or extrusion or by supporting it on a carrier and then using the resulting molding in the reaction.

The size of the molding as formed from said molybdenum oxide alone, from a mixture of said molybdenum oxide and a carrier, or from a mixture of said molybdenum oxide and said catalyst is generally about 3–10 mm, and the molding may take a variety of forms such as spheres, cylinders, rings, spoked rings and cloverleaf shapes, among others. Of course, said molybdenum oxide and said catalyst may be used in a powder form without being molded.

The amount of said molybdenum oxide in the reaction system as a whole is generally about 1–50 weight %, preferably about 3–20 weight %, based on the combined amount of said molybdenum oxide and said catalyst. The amount of the inert carrier with which molybdenum oxide may be molded as described above is generally 10–90% by weight of the combined amount of the molybdenum oxide and the carrier.

When the catalytic oxidation reaction is carried out in a fixed-bed reactor, the amount of said molybdenum oxide present in the reactant gas inlet region is generally about 5–50 weight %, preferably about 10–30 weight %, based on the total amount of said molybdenum oxide and said catalyst in the reaction zone. Herein, the term "reactant gas inlet region" as used with reference to a fixed-bed reactor means the region from 0– 20% to 0–50% of the length of the reaction zone and adjacent to the reactor inlet from which propylene, isobutylene or tertiary butanol is supplied, wherein the reaction zone ranges from the reactor inlet to the reactor outlet from which the reaction product and waste gas are withdrawn.

In the fixed-bed reactor which is conventionally employed for the commercial gas-phase catalytic oxidation of olefins, when the catalyst is used for a long period of time, the molybdenum content in the surface of said catalyst present in the reactant gas inlet region reduces with time, and the decreases in the selectivity and in the catalytic activity of said catalyst present in the inlet region tend to be greater, compared with those observed in the remainder of the reaction zone. Therefore, when such a fixed-bed reactor is used, so far as said molybdenum oxide is present in conjuction with said catalyst at least in the reactant gas inlet region, there is no particular restriction on the position of said molybdenum oxide and on the method how said molybdenum oxide is placed in the fixed-bed reactor.

Thus, said molybdenum oxide may be distributed throughout the entire catalyst bed or may be present only in the reactant gas inlet region. The reactor may be packed with a mixture of said catalyst and said molybdenum oxide in such a manner that the concentration of said molybdenum oxide in the mixture varies continuously or stepwise, and in this case, it is more effective to increase the concentration of said catalyst (i.e., to decrease the concentration of said molybdenum oxide) continuously or stepwise from the gas inlet to the gas outlet.

By using said molybdenum oxide in combination with said catalyst, the deterioration of said catalyst present in the reactant gas inlet region, where the deterioration occurs most severely in the absence of said molybdenum oxide, can be successfully inhibited for a long period, and additionally the evolution of heat in the reactant gas inlet region is suppressed because the composite oxide is diluted with said molybdenum oxide, and therefore advantageous effects such as inhibition of excessive oxidation and improvement in selectivity are achieved, with the result that an enhanced productivity per unit amount of the composite oxide is realized.

The gas phase catalytic oxidation of propylene, isobutylene or tertiary butanol with molecular oxygen can be carried out under the conventional reaction conditions. By way of example, the reaction temperature is usually 280°–400° C., preferably 300°–360° C. The reaction may be carried out under reduced pressure, but the reaction pressure preferably ranges from atmospheric pressure to 5 atm. The molar ratio of oxygen to propylene, isobutylene or tertiary butanol is usually 1–3, preferably 1.5–2.5. The space velocity is usually in the range of SV=500–5000/H.

For safety's sake, the reactant is preferably diluted with nitrogen, a rare gas such as argon, carbon dioxide, a lower alkane such as methane or propane, steam or the like.

The concentration of propylene, isobutylene or tertiary butanol for use in the reaction is usually about 3–15 volume % based on the total amount of the fed gases inclusive of the diluent gas.

The source of molecular oxygen for the reaction may be pure oxygen but, for commercial purposes, air or oxygen-enriched air is preferred.

As mentioned above, the present invention also provides a method of reuse of the calalyst comprising composite oxide represented by formula (1) which has been deteriorated due to the gas phase calalytic oxidation (hereinafter this term may sometimes be referred to simply as "said deteriorated catalyst"). The method of reuse of said deteriorated catalyst will be described below.

Thus, in the gas phase catalytic oxidation of propylene, isobutylene or tertiary butanol with molecular oxygen in the presence of said catalyst to give the corresponding unsaturated aldehyde and unsaturated carboxylic acid, the activity of the catalyst, which has been deteriorated due to said oxidation reaction, can be regenerated to restore and preserve the initial performance of said catalyst for a long period of time by mixing said deteriorated catalyst with said molybdenum oxide and using the mixture for the reaction.

As mentioned, the catalyst suffers decrease in catalytic activity and selectivity with time as the reaction is continued for a prolonged period of time. Therefore, according to the present invention, when a fixed-bed multi-tubular reactor, for instance, is used, the catalyst which has been deteriorated due to the gas phase catalytic oxidation is withdrawn from the reactor tubes, mixed with said molybdenum oxide and returned to the reactor tubes, whereby said deteriorated catalyst is regenerated and the reaction can be further continued with high productivity.

Said molybdenum oxide which can be used for this purpose may be any of those described hereinbefore which in itself are substantially inert to the gas phase catalytic oxidation reaction.

The deteriorated catalyst usable in the present invention may, for example, be one derived from said catalyst comprising the composite oxide of the formula (1), one derived from a mixture of said catalyst and said molybdenum oxide, one regenerated in accordance with the present invention, reused and deteriorated again, etc., and therefore said deteriorated catalyst can be reused repeatedly.

The method how said deteriorated catalyst is reused is not particularly limited. Thus, said deteriorated catalyst which has undergone deterioration due to the gas phase catalytic oxidation reaction is mixed with said molybdenum oxide in various manners, and then the mixture is used again as catalyst.

For example, said deteriorated catalyst is withdrawn from the tubular reactor, pulverized and mixed with a powder of said molybdenum oxide, and the mixture is molded by compression-molding, extrusion-molding or by being supported on a carrier, and then the moldings are placed in the reactor tubes. The moldings need not be calcined, but when water or an organic substance is used as a molding auxiliary during the molding operation, the moldings are preferably calcined in air or in an inert gas atmosphere within a temperature range of 400°–530° C., which is a conventionally employed calcining temperature range used in preparing fresh catalyst comprising composite oxide of the formula (1).

An alternative method of reuse comprises molding said molybdenum oxide singly or together with an inert carrier such as silica by compression, extrusion or impregnation, mixing the resultant molded product with said deteriorated catalyst moldings withdrawn from the reactor tubes, and re-packing the reactor tube with the mixture.

The amount of said molybdenum oxide to be mixed with said deteriorated catalyst by said gas phase oxidation reaction is not so critical, but when a powder of said molybdenum oxide is mixed with said pulverized deteriorated catalyst and the mixture is molded for reuse, the amount of said molybdenum oxide may be generally about 3–20 weight %, preferably about 5–15 weight %, based on said deteriorated catalyst. When the molding of said molybdenum oxide alone or the molding of a mixture of said molybdenum oxide and an inert carrier is blended with said deteriorated catalyst molding deteriorated by gas phase catalytic oxidation, said molybdenum oxide is generally used in an amount of about 5–40 volume %, preferably about 10–30 volume %, relative to said deteriorated catalyst, although the amount may vary depending on the shape of the moldings.

The size of the molding as formed from said molybdenum oxide alone, from a mixture of said molybdenum oxide and a carrier, or from a mixture of said molybdenum oxide and said deteriorated catalyst is generally about 3–10 mm, and the molding may take a variety of forms such as spheres, cylinders, rings, spoked rings and clover-leaf shapes, among others.

Where a fixed-bed multitubular reactor is used, the deterioration of the catalyst comprising composite oxide represented by the formula (1) due to the gas phase catalytic oxidation is more marked in the reactant gas inlet region and less marked or almost nil in the remainder of the reaction zone, as previously pointed out. Therefore, it is also a valid procedure to withdraw said deteriorated catalyst from the reactant gas inlet region only and blend it with said molybdenum oxide for reuse. Of course, said molybdenum oxide may additionally be blended with the less deteriorated portion or still perfectly active portion of said catalyst.

By using said molybdenum oxide in combination with said deteriorated catalyst, the deterioration of the catalyst present in the reactant gas inlet region, where the deterioration occurs most severely in the absence of said molybdenum oxide, can be successfully inhibited, and additionally the evolution of heat in the reactant gas inlet region is suppressed because the composite oxide is diluted with said molybdenum oxide, and therefore advantageous effects such as inhibition of excessive oxidation and improvement in selectivity are achieved, with the result that an enhanced productivity per unit amount of the composite oxide is realized.

For the purpose of said reuse, the reaction conditions for the gas phase catalytic oxidation of propylene, isobutylene or tertiary butanol with molecular oxygen in the presence of a mixture of said deteriorated catalyst and said molybdenum oxide may also be the same as the reaction conditions described hereinbefore.

The gas phase catalytic oxidation wherein a mixture of said deteriorated catalyst and said molybdenum oxide is used for reuse in accordance with this invention achieves the results which are comparable to those achieved by the gas phase catalytic oxidation wherein fresh catalyst comprising composite oxide represented by the formula (1) is used.

Typical advantages of the present invention can be summarized as follows.

In the invention, deterioration of said catalyst is well inhibited as compared with the case of using said catalyst alone, so long as said molybdenum oxide added remains in the reaction system, with the result that the catalytic activity is sustained over a long period of time.

In accordance with the method of this invention in which the gas phase catalytic oxidation reaction is conducted in the presence of said catalyst and said molybdenum oxide which in itself is substantially inert to the gas phase oxidation reaction, the deterioration of said catalyst associated with the gas phase catalytic oxidation of propylene, isobutylene or tertiary butanol can be inhibited for a longer period of time, compared with the known processes.

Furthermore, in the reuse method of this invention which comprises using a mixture of said deteriorated catalyst deteriorated by said gas phase catalytic oxidation reaction and said molybdenum oxide which in itself is substantially inert to said oxidation reaction, an activity equivalent to that of fresh catalyst comprising composite oxide of the formula (1) can be obtained with use of said deteriorated catalyst, and additionally the rate of the progress of catalyst deterioration is inhibited as compared with the rate observed when said catalyst alone is used, so that the catalyst can be used for a prolonged period of time.

Therefore, the industrial significance of these advantages is tremendous.

EXAMPLES

The following examples are intended to illustrate this invention in further detail and should by no means be construed as limiting the scope of the invention.

It should be understood that, in this specification, the conversion (%) and yield (%) are defined as follows.

$$\text{Conversion (\%)} = \frac{\text{(Number of moles of reacted olefin equivalent)}}{\text{(Number of moles of feed olefin equivalent)}} \times 100$$

$$\text{Selectivity (\%)} = \text{(Number of moles of products/number of moles of reactant olefin equivalent)} \times 100$$

$$\text{Yield (\%)} = \frac{\text{(Number of moles of product)} \times 100}{\text{(Number of moles of feed olefin equivalent)}}$$

In the above, the term "feed olefin equivalent" means propylene, isobutylene or tertiary butanol.

Example 1

Preparation of Catalyst

In 470 ml of warm water was dissolved 144 g of ammonium molybdate $[(NH_4)_6Mo_7O_{24}\cdot 4H_2O]$ followed by addition of 20.4 g of 20% silica sol $(SiO_2)$ to give Solution A. On the other hand, 2 g of nickel nitrate $[Ni(NO_3)_2\cdot 6H_2O]$, 138.5 g of cobalt nitrate $[Co(NO_3)_2\cdot 6H_2O]$, 55 g of ferric nitrate $[Fe(NO_3)_3\cdot 9H_2O]$ and 3.3 g of thallium nitrate $(TlNO_3)$ were dissolved in 250 ml of warm water to give Solution B. After 9.4 g of 60% nitric acid was added to 40 ml of purified water, 33 g of bismuth nitrate $[Bi(NO_3)_3\cdot 5H_2O)]$ was give Solution C. Then, Solution B was mixed with Solution C.

The mixture of Solutions B and C was added to Solution A which was stirred, and then 0.8 g of phosphoric acid $(H_3PO_4)$ was added thereto to give a slurry. The slurry was concentrated to dryness and subjected to nitrate salt decomposition in a stream of air at 200°–250° C. This product was pulverized and compressed into rings measuring 5 mm (outside diameter)×2 mm (inside diameter)×5 mm (height), which were then calcined in air at 480° C. to provide a catalyst comprising composite oxide.

The composition of the composite oxide was $Mo_{12}Bi_1Fe_2Ni_{0.1}Co_7Tl_{0.18}P_{0.1}Si_1$ (exclusive of oxygen; the same mode of representation applies hereinafter).

Separately, 100 g of ammonium molybdate $[(NH_4)_6Mo_7O_{24}\cdot 4H_2O]$ was calcined in air at 650° C. for 6 hours to prepare $MoO_3$, which was substantially inert to the gas phase catalytic oxidation.

Reaction

A glass reaction tube having an inside diameter of 18 mm was packed with 3 ml of the above catalyst and 1 g of said $MoO_3$ prepared above (6–10 mesh). In packing the tube, 20 g of 14-mesh silicon carbide was used for dilution in such a manner that there would be substantially no temperature gradient and that the catalyst and said $MoO_3$ would be almost homogenously distributed.

Then, an accelerated test reaction was carried out under the following conditions: reaction temperature=410° C., a propylene/air/steam molar ratio=1/7.5/3, and SV=3400/H. inlet pressure=1.0 atm.

The results are shown in Table 1.

Comparison Example 1

The procedure of Example 1 was repeated except that said $MoO_3$ was not used. The results are shown in Table 1. Comparison of the results of Example 1 with those of Comparison Example 1 indicates that the presence of said $MoO_3$ has an inhibitory effect on the deterioration of catalyst activity.

Comparison Example 2

The procedure of Example 1 was repeated except that $MoO_3$ prepared by calcining ammonium molybdate in air at 500° C. for 6 hours was used in place of the said $MoO_3$ prepared by calcining ammonium molybdate in air at 650° C. The results are shown in Table 1.

When MoO$_3$ prepared by calcining ammonium molybdate at 500° C. was employed, the selectivity was unsatisfactorily low even in the initial period of the reaction.

TABLE 1

|  | Reaction time (days) | Conversion of propylene (%) | Selectivity of acrolein and acrylic acid (%) |
|---|---|---|---|
| Example 1 | 5 | 78.0 | 94.2 |
|  | 50 | 75.5 | 96.5 |
|  | 200 | 69.2 | 97.1 |
| Comparison Example 1 | 5 | 78.2 | 94.0 |
|  | 50 | 72.2 | 94.8 |
|  | 100 | 59.8 | 95.8 |
| Comparison Example 2 | 5 | 80.5 | 90.2 |
|  | 50 | 76.6 | 91.2 |

Reference Example 1

Ammonium molybdate [(NH$_4$)$_6$Mo$_7$O$_{24}$·4H$_2$O] was calcined in air at 350° C. for 3 hours to give MoO$_3$. A small amount of water and 1.5% of stearic acid was added thereto, and the mixture was compressed into rings measuring 5 mm (outside diameter)×2 mm (inside diameter)×5 mm (height). The rings were then calcined at 630° C. in air for 6 hours.

A reaction tube having an inside diameter of 18 mm was packed with 10 ml of the above rings, and the reaction was carried out under the following conditions: reaction temperature=360°–420° C., a propylene/air/steam molar ratio=1/7.5/3 and a space velocity of SV=1100/H.

The conversion of propylene was invariably less than 0.5%, indicating that the starting propylene had undergone substantially no reaction.

Reference Example 2

MoO$_3$ was prepared in the same manner as described in Reference Example 1 except that the calcination of the rings was carried out at 500° for 6 hours, and then using this MoO$_3$, an experiment was performed in the same manner as in Reference Example 1. The results are shown in Table 2.

It is clear that the calcining temperature of 500° C. is insufficient to prepare an inert MoO$_3$.

TABLE 2

| No. | Reaction temperature (°C.) | Conversion of propylene (%) | Selectivity of acrolein and acrylic acid (%) |
|---|---|---|---|
| 1 | 360 | 14 | 21 |
| 2 | 380 | 21 | 18 |
| 3 | 400 | 35 | 17 |
| 4 | 420 | 55 | 12 |

Example 2

Preparation of Catalyst

The procedure of Example 1 was repeated down to the stage of nitrate salt decomposition and pulverization except that the use of nickel nitrate and phosphoric acid was omitted, that cesium nitrate (CsNO$_3$) was used in place of thallium nitrate, and that the scale of preparation was increased 80-fold, whereby a catalyst precursor was obtained. Separately, a commercially available MoO$_3$ was calcined at 630° C. for 6 hours.

Fifty-five (55) parts of the above catalyst precursor was mixed with 45 parts of said MoO$_3$ and the mixture was extrusion-molded in the conventional manner and calcined at 480° C. in air for 6 hours to provide Catalyst A. On the other hand, the same catalyst precursor used alone without addition of MoO$_3$ was similarly extrusion-molded and calcined at 480° C. in air to provide Catalyst B.

Composition of Catalyst A:

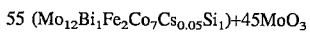

55 (Mo$_{12}$Bi$_1$Fe$_2$Co$_7$Cs$_{0.05}$Si$_1$)+45MoO$_3$

Composition of Catalyst B:

Mo$_{12}$Bi$_1$Fe$_2$Co$_7$Cs$_{0.05}$Si$_1$

Reaction

A reaction tube having an inside diameter of 30 mm was packed with 1.15 liters of Catalyst A as the catalyst to be placed in the reactant gas inlet region and, then, the remaining portion of the tube was packed with 2.3 liters of Catalyst B. With the temperature of the heating medium around the reaction tube being controlled at 325° C., the reaction was carried out at a propylene/air/nitrogen/steam molar ratio of 1/8/3/1.5, a space velocity of SV=1300/H, and an inlet pressure of 2.8 atm. The results are shown in Table 3.

After about one year of use, the catalyst was withdrawn, and using 10 ml portion of the catalyst which had been present in the inlet region or using 10 ml portion of the catalyst which had been present in the outlet region, the reaction was carried out under the same conditions as above. The results are shown in Table 4.

Comparison Example 3

The reactant gas inlet region of a tubular reactor was packed with 1.15 liters of a mixture of 45% porcelain Raschig rings and 55% Catalyst B obtained in Example 2 and, then, 2.3 liters of said Catalyst B was packed in the remaining portion of the tubular reactor.

The reaction was conducted under the same conditions as in Example 2 except that the reaction temperature was set at 327° C. The results are shown in Table 3.

In the same manner as in Example 2, a 10 ml portion each of the catalyst samples taken from the inlet and outlet regions was evaluated. The results are shown in Table 4.

When the catalyst according to the invention (catalyst comprising composite oxide+MoO$_3$) is used for about 1 year in the process of this invention, no decrease in selectivity is observed with respect to the catalyst in the inlet and outlet regions of the reactor.

On the other hand, when MoO$_3$ was not employed, the selectivity decreases with respect to the catalyst in the inlet region.

TABLE 3

|  | Reaction time (days) | Conversion of propylene (%) | Selectivity of acrolein and acrylic acid (%) |
|---|---|---|---|
| Example 2 | 21 | 97.8 | 93.9 |
|  | 330 | 97.7 | 94.0 |
| Comparison Example 3 | 21 | 97.7 | 94.0 |
|  | 330 | 97.4 | 92.9 |

TABLE 4

| | Sampling point | Conversion of propylene (%) | Selectivity of acrolein and acrylic acid (%) |
|---|---|---|---|
| Example 2 | Inlet region | 97.5 | 93.8 |
| | Outlet region | 97.7 | 94.1 |
| Comparison Example 3 | Inlet region | 97.7 | 91.0 |
| | Outlet region | 97.6 | 93.9 |

Example 3

Preparation of catalyst

Following the procedure described in Example 1, a composite oxide precursor was prepared.

The precursor was supported on α-Al$_2$O$_3$ (balls, 5 mm in diameter) (supporting ratio 30 wt. %) and calcined at 550° C. in air for 6 hours to obtain a catalyst comprising composite oxide represented by the formula $Mo_{12}Bi_{1.4}Fe_2Ni_5Co_4Tl_{0.5}P_{0.4}Si_{15}$.

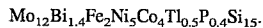

Separately, a commercial MoO$_3$ was calcined at 630° C. in air for 6 hours.

Reaction

A glass reaction tube having an inside diameter of 18 mm was packed with 12 ml of the above catalyst and 1 g of said MoO$_3$ prepared above (6–10 mesh). Said MoO$_3$ was packed in such a manner that it would be distributed almost uniformly throughout the catalyst bed.

A life test was performed with an isobutylene/air/steam molar ratio of 1/20/8 at a reaction temperature of 420° C. and a space velocity of SV=1500/H. The results are shown in Table 5.

Comparison Example 4

The procedure of Example 3 was repeated except that said MoO$_3$ was not employed. The results are shown in Table 5.

TABLE 5

| Example | Reaction time (days) | Conversion of isobutylene (%) | Selectivity of methacrolein and methacrylic acid (%) |
|---|---|---|---|
| Example 3 | 5 | 93.2 | 78.7 |
| | 50 | 94.1 | 79.8 |
| | 200 | 93.9 | 79.5 |
| Comparison Example 4 | 5 | 93.2 | 79.3 |
| | 50 | 94.6 | 75.5 |
| | 200 | 94.0 | 70.2 |

Example 4

In 470 liters of warm water was dissolved 144 kg of ammonium molybdate [(NH$_4$)$_6$Mo$_7$O$_{24}$.4H$_2$O] followed by addition of 20.4 kg of 20% silica sol (SiO$_2$) to prepare Solution A.

On the other hand, 138.5 kg of cobalt nitrate [Co(NO$_3$)$_2$.6H$_2$O], 55 kg of ferric nitrate [Fe(NO$_3$)$_3$.9H$_2$O] and 0.66 kg of cesium nitrate (CsNO$_3$) were dissolved in 250 liters of warm water to prepare Solution B.

After 9.4 kg of 60% nitric acid was added to 40 liters of purified water, 33 kg of bismuth nitrate [Bi(NO$_3$)$_3$.5H$_2$O] was dissolved to prepare Solution C.

Solution B was mixed with Solution C. With Solution A being stirred, the mixture of Solutions B and C was added to give a slurry. This slurry was concentrated to dryness and subject to nitrate salt decomposition at 200°–250° C. in a stream of air. The product was then pulverized and compressed into rings measuring 5 mm in outside diameter, 2 mm in inside diameter and 5 mm high, which were then calcined in air at 470° C. for 6 hours to provide a catalyst comprising composite oxide. The composition of this catalyst exclusive of oxygen was $Mo_{12}Bi_1Fe_2Co_7Cs_{0.05}Si_1$.

A glass reaction tube having an inside diameter of 18 mm was packed with 10 ml of the above fresh catalyst and the reaction was conducted by introducing a feed gas composed of propylene, air and steam having a propylene/air/steam molar ratio of 1/7.5/3 at a flow rate of SV=1100/H (standard condition). The reaction pressure was 2.0 atm.

The results of the reaction at a reaction temperature of 320° C. showed that the conversion of propylene was 97.5% and that the combined yield of acrolein and acrylic acid was 90.4%.

A reactor in an acrylic acid production plant was packed with the above fresh catalyst and the operation was continued for 3 years. Then, the catalyst in some reaction tubes was withdrawn and divided into 3 portions corresponding to the top, intermediate and bottom regions of each tube. When the catalyst in the gas inlet region was evaluated in the same manner as above, the conversion and yield were found to be 96.8% and 87.3%, respectively, indicating a significant decrease in yield. The results of evaluation of the catalyst withdrawn from the intermediate and outlet regions were almost comparable to the results obtained with use of the fresh catalyst.

In the following description, the deteriorated catalyst withdrawn from the reactant gas inlet region is referred to as "Deteriorated Catalyst A".

One-hundred (100) parts of a powder obtained by pulverizing Deteriorated Catalyst A was mixed with 10 parts of molybdenum trioxide obtained by calcining ammonium molybdate [(NH$_4$)$_6$Mo$_7$O$_{24}$.4H$_2$O] in air at 630° C. for 6 hours, and the mixture was compressed into rings measuring 5 mm in outside diameter, 2 mm in inside diameter and 5 mm in height, which were then calcined at 460° C. in air for 3 hours.

The activity of this catalyst was evaluated as above. The conversion was 97.0% and the yield was 90.3%, and these results were comparable to the results obtained with use of the fresh catalyst.

Example 5

One-hundred (100) parts of a powder prepared by pulverizing Deteriorated Catalyst A was mixed with 6 parts of a powder of commercial molybdenum trioxide (which had been confirmed to be inert in a trial oxidation of propylene) and 4 parts of ceramic fiber, followed by addition of water and methyl cellulose. The mixture was extruded into rings measuring 5 mm in outside diameter, 2 mm in inside diameter and a length of 6 mm, which were then calcined in air at 460° C. for 3 hours.

The activity of this catalyst was evaluated as in Example 4. The conversion was 97.2% and the yield was 90.4%, and these results were comparable to the results obtained with use of the fresh catalyst.

15

Comparison Example 5

Using an electric furnace, Deteriorated Catalyst A as such was calcined in air at 460° C. for 6 hours.

The activity of this catalyst was evaluated in the same manner as in Example 4. The conversion and yield were 96.5% and 88.7%, respectively. Thus, the catalyst was not sufficiently regenerated.

Example 6

A single-tube test was performed using the fresh catalyst prepared in Example 4. Thus, a carbon steel reaction tube having an inside diameter of 30 mm and having a length of 4 m was packed with the catalyst alone over the length of 2.8 m in the gas outlet region. Then, over a length of 1.2 m in the inlet region, a mixture of 70 volume % of the catalyst and 30 volume % of porcelain Raschig rings having an outside diameter of 6.2 mm was packed.

Then, the reaction was carried out by introducing a feed gas composed of propylene, air and steam having a propylene/air/steam molar ratio of 1/7.5/3 at a space velocity of SV=1000/H (standard condition). The gas inlet pressure was 1.1 kg/cm²G and the heating medium temperature was adjusted to 310° C.

The performance analysis conducted after 7 days of reaction showed a propylene conversion of 97.7%, an acrolein yield of 83.5% and an acrylic acid yield of 8.3%.

The operation was further continued using substantially the same reactant gas composition and SV as above but controlling the heating medium temperature so as to insure a conversion of 97.5–98.0%. After 650 days of operation, the performance analysis conducted at the heating medium temperature of 322° C. showed a propylene conversion of 97.6%, an acrolein yield of 80.2% and an acrylic acid yield of 8.8%.

The reaction was terminated at this stage and the diluted catalyst packed in the 1.2 m-long region on the gas inlet side was withdrawn. The Raschig rings were separated off from the catalyst by the use of a sieve. On the other hand, a commercial molybdenum trioxide was compression-molded into rings each measuring 6 mm in outside diameter, 2.5 mm in inside diameter and 6 mm high and calcined in air at 600° C. for 6 hours. The above catalyst (I) and this molded molybdenum trioxide (II) were mixed in a ratio of I:II=65:35 (vol. %) and the mixture was re-packed into said 1.2 m-long region.

The reaction was then re-started and the productivity was evaluated 2 days later. At the heating medium temperature of 313° C., the conversion of propylene was 97.6%, the yield of acrolein was 82.2%, and the yield of acrylic acid was 8.6%.

The reaction was further continued and the performance after 21 days was evaluated. At the heating medium temperature of 316° C., the conversion of propylene was 97.8%, the yield of acrolein was 83.8%, and the yield of acrylic acid was 8.1%. Thus, the yields were comparable to those obtained with the fresh catalyst.

The reaction was further continued. The results at the heating medium temperature of 323° C. on day 260 after repacking were as follows: the conversion of propylene= 97.6%, yield of acrolein=83.6%, yield of acrylic acid=8.2%. Thus, there was substantially no decrease in yield.

Example 7

A catalyst comprising composite oxide of the composition (exclusive of oxygen) $Mo_{12}Bi_{1.4}Fe_2Ni_5Co_4Tl_{0.5}P_{0.4}Si_{15}$ was prepared following the procedure described in Example 4. However, nickel nitrate [Ni(NO$_3$)$_2$.6H$_2$O] and thallium nitrate (TlNO$_3$) and phosphoric acid (H$_3$PO$_4$) were used as sources of Ni, Tl and P, respectively, and after nitrate salt decomposition and pulverization, the powder of the catalyst was supported on α-Al$_2$O$_3$ (balls, 5 mm in diameter) (supporting ratio 30 wt. %) and calcined in air at 550° C. for 6 hours.

A glass reaction tube having an inside diameter of 18 mm was packed with the above fresh catalyst (12 ml). Then, at a reaction temperature of 420° C., an accelerated life test was carried out with an isobutylene/air/steam molar ratio of 1/20/8 at SV=1500/H.

After 5 days of testing, the conversion of isobutylene was 93.2% and the selectivity of methacrolein and methacrylic acid was 79.3%. After 200 days, however, the conversion was 94.0% and the selectivity was 70.2%.

The deteriorated catalyst was withdrawn from the reaction tube and mixed with 3 ml of a 10–16 mesh powder obtained by pulverizing said inert molded molybdenum trioxide used in Example 3. The reaction tube was repacked with the resulting mixture and the reaction was re-started under the same conditions as above.

The converison and selectivity after 2 days were 93.5% and 75.6%, respectively. However, after 10 days, the converison and selectivity became 93.0% and 79.1%, respectively. Thus, a performance comparable to that of the fresh catalyst was achieved.

Comparison Example 6

In 200 ml of deionized water at 50° C. was dissolved 123 g of ammonium molybdate [(NH$_4$)$_6$Mo$_7$O$_{24}$.4H$_2$O], and 1000 g of Deteriorated Catalyst A was impregnated with the aqueous solution, dried and calcined in air at 350° C. for 6 hours. The amount of MoO$_3$ based on the deteriorated catalyst was 10 weight %.

The performance of this catalyst was evaluated in the same manner as in Example 4. The conversion was 97.3% and the yield was 88.4%. Thus, the catalyst was only partially regenerated.

Comparison Example 7

The procedure of Comparison Example 6 was repeated except that the calcination was performed at 550° C. The performance of this catalyst was evaluated in the same manner as in Example 4. The conversion and yield were 63.5% and 59.7%, respectively. Thus, the catalyst activity had dropped considerably.

What is claimed is:

1. A process for producing an unsaturated aldehyde and a carboxylic acid which comprises subjecting propylene, isobutylene or tertiary butanol to gas phase catalytic oxidation with molecular oxygen in the presence of (i) a catalyst comprising composite oxide represented by the formula

$$Mo_aBi_bFe_cA_dB_eC_fD_gO_x$$

wherein Mo, Bi, Fe and O represent molybdenum, bismuth, iron and oxygen, respectively; A represents nickel and/or cobalt; B represents at least one element selected from the group consisting of manganese, zinc, calcium, magnesium, tin and lead; C represents at least one element selected from the group consisting of phosphorus, boron, arsenic, tellurium, tungsten, antimony and silicon; D represents at least one element selected from the group consisting of potassium, rubidium, cesium and thallium; in case of a being 12, $0<b\leqq10$, $0<c\leqq10$, $1\leqq d\leqq10$, $0\leqq e\leqq10$, $0\leqq f\leqq20$ and $0<g\leqq2$; and x has a value dependent on the oxidation state of the respective elements and (ii) a molybdenum oxide which in itself is substantially inert to said gas phase catalytic oxidation to provide the corresponding unsaturated aldehyde and unsaturated carboxylic acid.

2. The process according to claim 1, wherein said unsaturated aldehyde and unsaturated carboxylic acid are either acrolein and acrylic acid or methacrolein and methacrylic acid.

3. The process according to claim 1, wherein said molybdenum oxide which in itself is substantially inert to said gas phase catalytic oxidation is a molybdenum oxide prepared by calcining a molybdenum compound in air at a temperature of 550°–700° C.

4. The process according to claim 1, wherein said catalyst and said molybdenum oxide which in itself is substantially inert to said gas phase catalytic oxidation is used in the form of a molding formed from a mixture of said catalyst and said molybdenum oxide.

5. The process according to claim 1, wherein said gas phase catalytic oxidation is conducted in a fixed-bed multitubular reactor.

6. The process according to claim 5, wherein said molybdenum oxide is present in the reactant gas inlet region of the fixed bed multitubular reactor.

7. A process for producing an unsaturated aldehyde end a carboxylic acid by subjecting propylene, isobutylene or tertiary butanol to gas phase catalytic oxidation with molecular oxygen in the presence of a catalyst comprising a composite oxide represented by the formula

wherein Mo, Bi, Fe and represent molybdenum, bismuth, iron and oxygen, respectively; A represents at least one element selected from the group consisting of nickel and cobalt; B represents at least one element selected from the group consisting of manganese, zinc, calcium, magnesium, tin and lead; C represents at least one element selected from the group consisting of phosphorus, boron, arsenic, tellurium, tungsten, antimony and silicon; D represents at least one element selected from the group consisting of potassium, rubidium, cesium and thallium; when a is 12, $0<b<10$, $0<c\leqq10$, $1\leqq d\leqq10$, $0\leqq e\leqq10$, $0\leqq f\leqq20$ and $0<g\leqq2$; and has a value dependent on the oxidation state of the respective elements, wherein the catalyst deteriorated due to said gas phase catalytic oxidation is reused after mixing it with a molybdenum oxide which in itself is substantially inert to said gas phase catalytic oxidation, and optionally calcining the resulting mixture at a temperature of from 400° to 530° C., wherein said gas phase catalytic oxidation reaction is conducted in a fixed-bed reactor.

8. The process according to claim 7, wherein said gas phase catalytic oxidation is conducted in a fixed bed multitubular reactor.

9. The process according to claim 8, wherein said mixing is effected by pulverizing the molded catalyst deteriorated due to said gas phase catalytic oxidation, blending it with a powder of said molybdenum oxide which in itself is substantially inert to said gas phase catalytic oxidation, and molding the mixture.

10. The process according to claim 8, wherein said mixing is effected by blending the molded catalyst deteriorated due to said gas phase catalytic oxidation with a molding containing said molybdenum oxide which in itself is substantially inert to said gas phase catalytic oxidation.

11. The process according to claim 9, wherein said molybdenum oxide which in itself is substantially inert to said gas phase catalytic oxidation is used in an amount of 3–20 weight percent based on the catalyst deteriorated due to said gas phase catalytic oxidation.

12. The process according to claim 10, wherein said molybdenum oxide which in itself is substantially inert to said gas phase catalytic oxidation is used in an amount of 5–40 volume % based on the catalyst deteriorated due to said gas phase catalytic oxidation.

13. The process according to claim 8, 9 or 10, wherein a portion of said catalyst which is present in a reactant gas inlet region and which has been deteriorated due to said gas phase catalytic oxidation is used in admixture with said molybdenum oxide which in itself is substantially inert to said gas phase catalytic oxidation.

14. A process for regenerating a catalyst consisting essentially of mixing (i) a catalyst comprising a composite oxide represented by the formula

wherein Mo, Bi, Fe and O represent molybdenum, bismuth, iron and oxygen, respectively; A represents at least one element selected from the group consisting of nickel and cobalt; B represents at least one element selected from the group consisting of manganese, zinc, calcium, magnesium, tin and lead; C represents at least one element selected from the group consisting of phosphorus, boron, arsenic, tellurium, tungsten, antimony and silicon; D represents a least one element selected from the group consisting of potassium, rubidium, cesium and thallium; when a is 12, $0<b\leqq10$, $0<c\leqq10$, $1\leqq d\leqq10$, $0\leqq e\leqq10$, $0\leqq f\leqq20$ and $0<g\leqq2$; and x has a value dependent on the oxidation state of the respective elements, wherein the catalyst has been used in and deteriorated due to a gas phase catalytic oxidation of propylene, isobutylene or tertiary butanol using molecular oxygen to provide a corresponding unsaturated aldehyde and unsaturated carboxylic acid, and (ii) a molybdenum oxide which in itself is substantially inert to said gas phase catalytic oxidation, and optionally calcining the resulting mixture of (i) and (ii) within a temperature range 400° to 530° C.

15. The process according to claim 3, wherein said molybdenum compound is ammonium molybdate or molybdenum trioxide.

16. The process according to claim 1, wherein said molybdenum oxide has a specific surface area of not more than about 2 m²/g measured by BET method or has an average particle size of about 1 μm or more measured by light scattering particle size analyzer.

17. The process according to claim 1, wherein the reaction is carried out at a temperature of 280° to 400° C.

18. The process according to claim 7, wherein said molybdenum oxide is obtained by calcining a molybdenum compound in air at a temperature of about 550° to 700° C.

19. The process according to claim 7, wherein said molybdenum compound is ammonium molybdate or molybdenum trioxide.

20. The process according to claim 7, wherein said molybdenum oxide has a specific surface area of not more than about 2 m²/g measured by BET method or has an average particle size of about 1 μm or more measured by light scattering particle size analyzer.

21. The process according to claim 7, wherein the reaction is carried out at a temperature of 280° to 400° C.

22. The process according to claim 14, wherein said molybdenum oxide is obtained by calcining a molybdenum compound at a temperature of about 550° to 700° C.

23. The process according to claim 22, wherein said molybdenum compound is ammonium molybdate or molybdenum trioxide.

24. The process according to claim 14, wherein said molybdenum oxide has a specific surface area of not more than about 2 $m^2/g$ measured by BET method or has an average particle size of about 1 μm or more measured by light scattering particle size analyzer.

25. The process according to claim 1, wherein a is 12, $0<b\leqq10$, $0<c\leqq10$, $1\leqq d\leqq10$, $0\leqq e\leqq10$, $0\leqq f\leqq10$ and $0<g\leqq2$; and x has a value dependent on the oxidation state of the respective elements.

26. The process according to claim 7, wherein a is 12, $0<b\leqq10$, $0<c\leqq10$, $1\leqq d\leqq10$, $0\leqq e\leqq10$, $0\leqq f\leqq10$ and $0<g\leqq2$; and x has a value dependent on the oxidation state of the respective elements.

27. The process according to claim 14, wherein a is 12, $0<b\leqq10$, $0<c\leqq10$, $1\leqq d\leqq10$, $0\leqq e\leqq10$, $0\leqq f\leqq10$ and $0<g\leqq2$; and x has a value dependent on the oxidation state of the respective elements.

28. The process according to claim 7, wherein said resulting mixture is calcined in air or in an inert gas atmosphere.

29. The process according to claim 14, wherein said resulting mixture is calcined in air or in an inert gas atmosphere.

* * * * *